United States Patent
Boutell et al.

(10) Patent No.: US 10,590,464 B2
(45) Date of Patent: Mar. 17, 2020

(54) ENHANCED UTILIZATION OF SURFACE PRIMERS IN CLUSTERS

(71) Applicant: ILLUMINA CAMBRIDGE LIMITED, Essex (GB)

(72) Inventors: Jonathan Mark Boutell, Essex (GB); Gary Mark Skinner, Essex (GB)

(73) Assignee: Illumina Cambridge Limited, Cambridge (GB)

( * ) Notice: Subject to any disclaimer, the term of this patent is extended or adjusted under 35 U.S.C. 154(b) by 94 days.

(21) Appl. No.: 15/576,211

(22) PCT Filed: May 27, 2016

(86) PCT No.: PCT/GB2016/051574
§ 371 (c)(1),
(2) Date: Nov. 21, 2017

(87) PCT Pub. No.: WO2016/193695
PCT Pub. Date: Dec. 8, 2016

(65) Prior Publication Data
US 2018/0142281 A1    May 24, 2018

Related U.S. Application Data

(60) Provisional application No. 62/168,602, filed on May 29, 2015.

(51) Int. Cl.
*C12Q 1/6806*    (2018.01)
*C12Q 1/6844*    (2018.01)
*C12P 19/34*    (2006.01)

(52) U.S. Cl.
CPC ......... *C12Q 1/6806* (2013.01); *C12Q 1/6844* (2013.01); *C12Q 2523/113* (2013.01);
(Continued)

(58) Field of Classification Search
None
See application file for complete search history.

(56) References Cited

U.S. PATENT DOCUMENTS

| 5,223,414 A | 6/1993 | Zarling et al. |
| 6,172,218 B1 | 1/2001 | Brenner |

(Continued)

FOREIGN PATENT DOCUMENTS

| CN | 103 388 024 A | 11/2013 |
| GB | 2377220 | 8/2004 |

(Continued)

OTHER PUBLICATIONS

Cockroft et al. 2008. A single-molecule nanopore device detects DNA polymerase activity with single-nucleotide resolution. *J. Am. Chem. Soc.*, 130(3):818-820.
(Continued)

*Primary Examiner* — Young J Kim
(74) *Attorney, Agent, or Firm* — Knobbe, Martens, Olson & Bear, LLP

(57) ABSTRACT

Presented herein are methods and compositions for enhancing utilization of surface primers during the surface amplification process. The methods are useful for surface amplification at improved densities. The methods and compositions provided herein enable creation of clusters which are brighter, but at the same densities as currently achieved using standard cluster amplification.

15 Claims, 6 Drawing Sheets

(52) U.S. Cl.
CPC . *C12Q 2523/305* (2013.01); *C12Q 2525/131* (2013.01); *C12Q 2535/122* (2013.01); *C12Q 2565/543* (2013.01)

(56) References Cited

U.S. PATENT DOCUMENTS

| | | |
|---|---|---|
| 6,258,568 B1 | 7/2001 | Nyren |
| 6,274,320 B1 | 8/2001 | Rothberg et al. |
| 6,306,597 B1 | 10/2001 | Macevicz |
| 6,737,236 B1 | 5/2004 | Pieken et al. |
| 6,969,488 B2 | 11/2005 | Bridgham et al. |
| 7,001,792 B2 | 2/2006 | Sauer et al. |
| 7,057,026 B2 | 6/2006 | Barnes et al. |
| 7,115,400 B1 | 10/2006 | Adessi et al. |
| 7,211,414 B2 | 5/2007 | Hardin et al. |
| 7,259,258 B2 | 8/2007 | Kozlov et al. |
| 7,315,019 B2 | 1/2008 | Turner et al. |
| 7,329,492 B2 | 2/2008 | Hardin et al. |
| 7,375,234 B2 | 5/2008 | Sharpless et al. |
| 7,399,590 B2 | 7/2008 | Piepenburg et al. |
| 7,427,673 B2 | 9/2008 | Balasubramanian et al. |
| 7,427,678 B2 | 9/2008 | Pieken et al. |
| 7,754,429 B2 | 7/2010 | Rigatti et al. |
| 7,829,284 B2 | 11/2010 | Kong et al. |
| 7,985,565 B2 | 7/2011 | Mayer et al. |
| 8,017,335 B2 | 9/2011 | Smith |
| 8,192,930 B2 | 6/2012 | Vermaas et al. |
| 8,715,966 B2 | 5/2014 | Liu et al. |
| 2005/0100900 A1 | 5/2005 | Kawashima et al. |
| 2006/0188901 A1 | 8/2006 | Barnes et al. |
| 2006/0240439 A1 | 10/2006 | Smith et al. |
| 2006/0281109 A1 | 12/2006 | Barr Ost et al. |
| 2007/0166705 A1 | 7/2007 | Milton et al. |
| 2008/0108082 A1 | 5/2008 | Rank et al. |
| 2008/0280773 A1 | 11/2008 | Fedurco et al. |
| 2008/0318244 A1 | 12/2008 | Matsunaga et al. |
| 2009/0026082 A1 | 1/2009 | Rothberg et al. |
| 2009/0118128 A1* | 5/2009 | Liu .................... C12Q 1/6806 506/2 |
| 2009/0127589 A1 | 5/2009 | Rothberg et al. |
| 2010/0111768 A1 | 5/2010 | Banerjee et al. |
| 2010/0137143 A1 | 6/2010 | Rothberg et al. |
| 2010/0282617 A1 | 11/2010 | Rothberg et al. |
| 2011/0059865 A1 | 3/2011 | Smith et al. |
| 2012/0156728 A1 | 6/2012 | Li et al. |
| 2012/0270305 A1 | 10/2012 | Reed et al. |
| 2012/0316086 A1 | 12/2012 | Lin et al. |
| 2013/0079232 A1 | 3/2013 | Kain et al. |
| 2013/0116153 A1 | 5/2013 | Bowen et al. |
| 2013/0203607 A1 | 8/2013 | Li et al. |
| 2013/0225421 A1 | 8/2013 | Li et al. |
| 2013/0260372 A1 | 10/2013 | Buermann et al. |
| 2013/0338042 A1 | 12/2013 | Shen et al. |
| 2014/0079923 A1 | 3/2014 | George et al. |
| 2014/0296109 A1 | 10/2014 | Rigatti et al. |
| 2014/0349891 A1 | 11/2014 | Liu et al. |

FOREIGN PATENT DOCUMENTS

| | | |
|---|---|---|
| WO | WO 91/06678 A1 | 5/1991 |
| WO | WO 01/48242 | 7/2001 |
| WO | WO 2004/018497 A2 | 3/2004 |
| WO | WO 2005/065814 A1 | 7/2005 |
| WO | WO 2006/064199 A1 | 6/2006 |
| WO | WO 2007/010251 A2 | 1/2007 |
| WO | WO 2007/123744 A2 | 11/2007 |
| WO | WO 14/108810 | 7/2014 |

OTHER PUBLICATIONS

Deamer et al. 2000. Nanopores and nucleic acids: Prospects for ultrarapid sequencing. *Trends Biotechnol.*, 18:147-151.
Deamer et al. 2002. Characterization of nucleic acids by nanopore analysis. *Acc. Chem. Res.*, 35:817-825.
Healy, K. 2007. Nanopore-based single-molecule DNA analysis. *Nanomedicine*, 2(4):459-481.
Korlach et al. 2008. Selective aluminum passivation for targeted immobilization of single DNA polymerase molecules in zero-mode waveguide nano structures. *Proc. Natl. Acad. Sci. USA*, 105(4):1176-1181.
Levene et al. 2003. Zero-mode waveguides for single-molecule analysis at high concentrations. *Science*, 299:682-686.
Li et al. 2003. DNA molecules and configurations in a solid-state nanopore microscope. *Nature Materials*, 2:611-615.
Lundquist et al. 2008. Parallel confocal detection of single molecules in real time. *Optics Letters*, 33(9):1026-1028.
Metzker, M. 2005. Emerging technologies in DNA sequencing. *Genome Research*, 15:1767-1776.
Ronaghi et al. 1996. Real-time DNA sequencing using detection of pyrophosphate release. *Analytical Biochemistry*, 242(1):84-89.
Ronaghi et al. 1998. A sequencing method based on real-time pyrophosphate. *Science*, 281(5375):363-365.
Ronaghi, M. 2001. Pyrosequencing sheds light on DNA sequencing. *Genome Research*, 11:3-11.
Ruparel et al. 2005. Design and synthesis of a 3'-O-allyl photocleavable fluorescent nucleotide as a reversible terminator for DNA sequencing by synthesis. *Proc Natl Acad Sci USA*, 102(17):5932-5937.
Soni et al. 2007. Progress toward ultrafast DNA sequencing using solid-state nanopores. *Clinical Chemistry*, 53(11):1996-2001.
International Search Report dated Aug. 2, 2016 for International Application No. PCT/GB2016/051574 filed May 27, 2016, 4 pages.
International Preliminary Report on Patentability (Chapter I) dated Dec. 5, 2017 for International Application No. PCT/GB2016/051574 filed May 27, 2016, 7 pages.

* cited by examiner

ENHANCED UTILIZATION OF SURFACE PRIMERS IN CLUSTERS

This application is the U.S. National Phase of Application No. PCT/GB2016/051574 entitled "ENHANCED UTILIZATION OF SURFACE PRIMERS IN CLUSTERS" filed May 27, 2016, which designated the United States, and which claims the benefit of U.S. Provisional Application No. 62/168,602, filed May 29, 2015, which is hereby incorporated by reference in its entirety and for all purposes.

BACKGROUND

The task of cataloguing human genetic variation and correlating this variation with susceptibility to disease is daunting and expensive. A drastic reduction in this cost is imperative for advancing the understanding of health and disease. A reduction in sequencing costs will require a number of technical advances in the field. Technical advances that could reduce the cost of genome analysis include: (1) library generation; (2) highly-parallel clonal amplification and analysis; (3) development of robust cycle sequencing biochemistry; (4) development of ultrafast imaging technology; and (5) development of algorithms for sequence assembly from short reads.

The creation of clonal amplifications in a highly-parallel manner is important for cost-effective sequencing. Sequencing is generally performed on clonal populations of DNA molecules traditionally prepared from plasmids grown from picking individual bacterial colonies. In the human genome project, each clone was individually picked, grown-up, and the DNA extracted or amplified out of the clone. In recent years, there have been a number of innovations to enable highly-parallelized analysis of DNA clones particularly using array-based approaches. In the simplest approach, the library can be analyzed at the single molecule level which by its very nature is clonal. The major advantage of single molecule sequencing is that cyclic sequencing can occur asynchronously since each molecule is read out individually. In contrast, analysis of clonal amplifications requires near quantitative completion of each sequencing cycle, otherwise background noise progressively grows with each ensuing cycle severely limiting read length. As such, clonal analysis places a bigger burden on the robustness of the sequencing biochemistry and may potentially limit read lengths.

Thus, there exists a need to develop methods to improve genomics analysis and provide more cost effective methods for sequence analysis. The present invention satisfies this need and provides related advantages as well.

BRIEF SUMMARY

The methods and compositions provided herein enable surface amplification at improved densities. Described herein are methods for enhancing utilization of surface primers during the surface amplification process. The methods are useful for surface amplification at improved densities. The methods and compositions provided herein enable creation of clusters which are brighter, but at the same densities as currently achieved using standard cluster amplification. Brighter clusters may have a number of advantages, for example, better quality of reads, support for longer read lengths, faster scan times for sequencing, and increased system robustness.

Presented herein are methods and compositions for preparing immobilized templates for a nucleic acid sequencing reaction comprising: (a) providing a solid support having a plurality of forward and reverse amplification primers immobilized thereon, wherein a subset of the plurality of amplification primers comprises a cleavage site; (b) amplifying a template using the subset of primers on the support to produce a plurality of double-stranded nucleic acid molecules, wherein both strands of each double-stranded nucleic acid molecule are attached to the solid support at their 5' ends; (c) cleaving the subset of primers at the cleavage site; and (d) subjecting the cleaved strand to partially-denaturing conditions to facilitate hybridization of a portion of the non-immobilized strand of the amplification product with the complementary immobilized amplification primer, followed by extension of the immobilized amplification primer to generate a copy of the non-immobilized strand of the amplification product.

In some embodiments, the partially-denaturing conditions comprise adding one or more components of a recombinase/polymerase amplification reaction to facilitate strand invasion. In some embodiments, the partially-denaturing conditions comprise subjecting the template to conditions suitable for template walking.

In some embodiments, step (d) comprises applying primers in solution to facilitate hybridization of the primers to the non-immobilized end of the immobilized amplification product.

The details of one or more embodiments are set forth in the accompanying drawings and the description below. Other features, objects, and advantages will be apparent from the description and drawings, and from the claims.

DETAILED DESCRIPTION

Presented herein are methods and compositions for enhancing utilization of surface primers during the surface amplification process. The methods are useful for surface amplification at improved densities. The methods and compositions provided herein enable creation of clusters which are brighter, but at the same densities as currently achieved using standard cluster amplification.

Currently available sequencing technologies utilize surface amplification to form clusters of amplified nucleic acid on a solid support. The most common approaches include bridge amplification and isothermal amplification can be performed using kinetic exclusion amplification (KEA), also referred to as exclusion amplification (ExAmp). Both of these amplification methodologies utilize 2 different surface primers, forward and reverse, immobilized on a solid support. However, both bridge and ExAmp cluster amplification processes make inefficient use of the 2 surface primers. Current estimates are that <10% of the surface primers are converted into template strands after amplification. A need exists for improved methods of surface amplification witch enable more robust utilization of existing surface primers. Methods that can utilise a greater fraction of the surface primers would provide great benefits in terms of brightness of the resulting clusters during sequencing and enhanced sequencing quality in signal-limited sequencing platforms.

Presented herein are methods for enhancing the occupancy of surface primers, enabling clusters with a higher density of nucleic acid amplification product, and resulting in greatly improved signal during sequencing by synthesis. In certain embodiments presented herein, the amplification methods comprise performing a standard bridge or ExAmp amplification procedure. After the standard amplification is complete, one of the two surface primers is cleaved and removed from the solid support. The amplified molecules remain constrained at only one end, but left in dsDNA form. A subsequent round of amplification then takes place under partially denaturing conditions to facilitate hybridization of a portion of the non-immobilized strand of the amplification product with the complementary immobilized amplification primer, followed by extension of the immobilized amplification primer to generate a copy of the non-immobilized strand of the amplification product.

Figure 1:
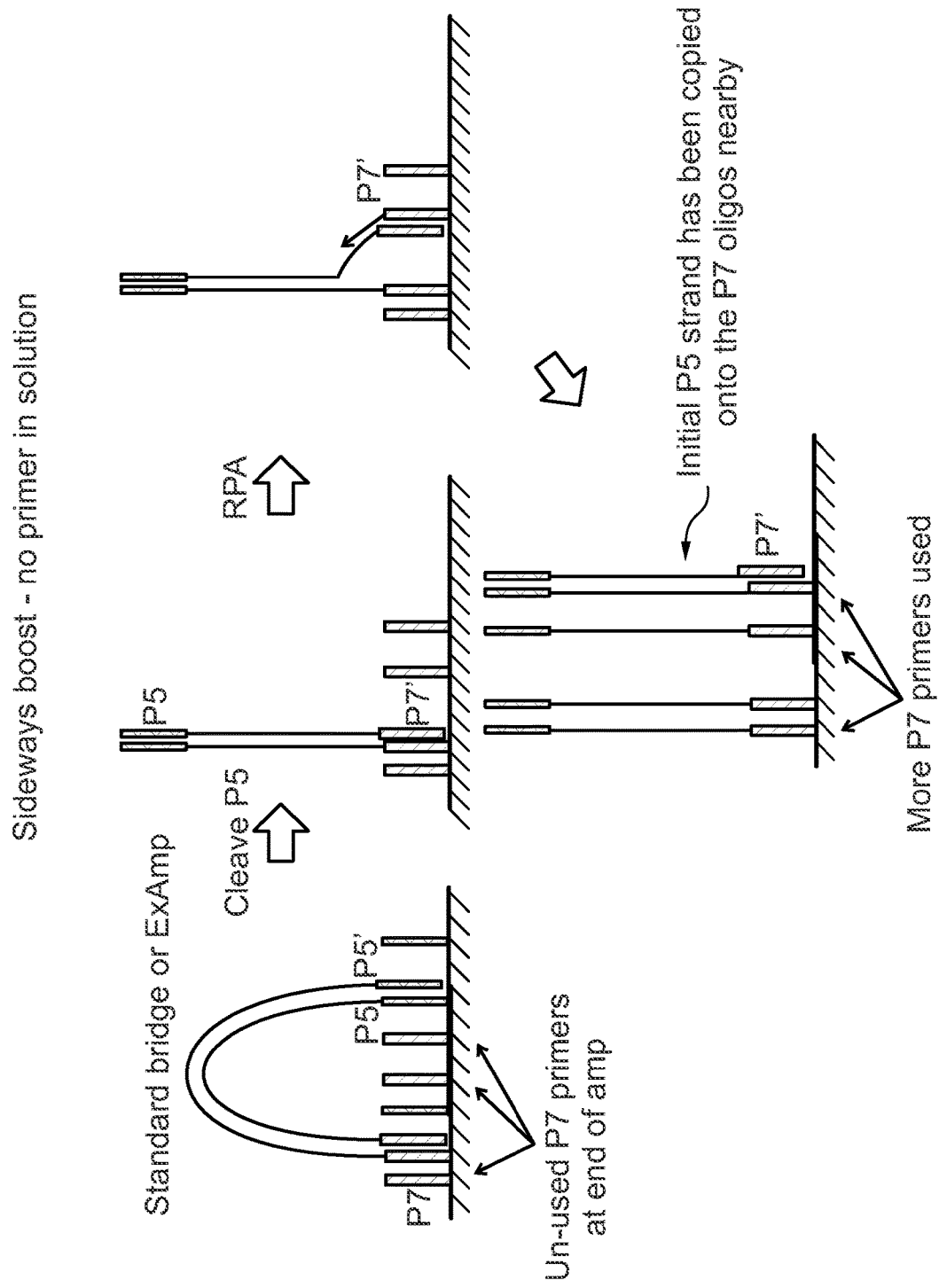
FIG. 1 is a schematic showing an amplification method according to one embodiment.

A general depiction of the method according to one embodiment is illustrated in FIG. 1. As shown in FIG. 1, an initial surface amplification process is performed with both forward primers and reverse primers present on the surface. Forward and reverse primers are designated in FIG. 1 as "P7" and "P5", although it will be appreciated that the methods presented herein can be performed with any surface-bound forward and reverse amplification primers. The initial surface amplification process can be performed using any suitable amplification procedure known in the art, for example, via bridge amplification or recombinase/polymerase amplification (RPA), also referred to as ExAmp in FIG. 1. Following the initial round of amplification, a large portion of the surface-bound forward and reverse primers remain unextended. While not wishing to be bound by theory, the low utilization of surface primers during bridge and/or RPA amplification may be due to steric hindrance or other physical constraints due to the need for the template molecules to "bridge" over to the 2 surface primers.

Next, as illustrated in FIG. 1, a subset of the surface-bound primers is cleaved from the surface. The subset of surface-bound primers that are cleaved can be, for example, the forward primers, or alternatively, the reverse primers. It will be appreciated that in some embodiments, not all of the forward or reverse primers will be cleaved from the surface. For example, after cleavage of reverse primers (P5), a portion of P5 primers may still remain bound to the surface. In some embodiments, less than 90%, 80%, 70%, 60%, 50%, 40%, 30%, 20%, 10%, or less than 5% of the originally bound forward primers remain bound to the surface. In some embodiments, less than 90%, 80%, 70%, 60%, 50%, 40%, 30%, 20%, 10%, or less than 5% of the originally bound reverse primers remain bound to the surface.

In the embodiment shown in FIG. 1, the cleavage step cleaves both unextended and extended P5 primers. Thus, after cleavage, some of the cleaved primers remain tethered to the solid support via the linearized bridge structure. Cleaved, unextended primers will be in solution and can be removed from the solid support by a washing step if desired.

Although the terms P5 and P7 are used throughout the instant description to refer to reverse and forward primers, it will be appreciated that the methods presented herein are not limited to cleavage of only reverse primers. In alternative embodiments to those described in the figures, the forward primer can be cleaved, leaving the reverse primer immobilized on the solid support.

Any one of a number of cleavable oligonucleotide, cleavable linker and cleavage approaches can be utilized in the methods presented herein. Methods for cleaving oligonucleotides from a solid support are known in the art, as exemplified by the disclosure of U.S. Pat. No. 8,715,966, which is incorporated by reference in its entirety. For example, oligonucleotide primers can be cleaved via chemical, photochemical, enzymatic, or any other suitable methodology which cleaves all or a portion of an oligonucleotide primer from the solid support. A cleavage site can be, for example, positioned into a pre-determined site during oligonucleotide synthesis. In some embodiments, chemical cleavage can be achieved by incorporating one or more diol units into the primer during oligonucleotide synthesis, or into a linker that connects the oligonucleotide to the solid support, and then treating the diol-containing oligonucleotide with a chemical cleavage agent such as periodate. In some embodiments, enzymatic cleavage can occur by any enzyme that can nick or cleave the immobilized oligonucleotide. In some embodiments, a restriction endonuclease or nicking endonuclease can be used. In some embodiments, an abasic site can be generated in the oligonucleotide by incorporating deoxyuridine (U) or any other non-natural or modified deoxyribonucleotide as described in the incorporated materials of U.S. Pat. No. 8,715,966. For example, deoxyuridine (U), 8-oxoguanine, or deoxyinosine can be incorporated into a pre-determined site during oligonucleotide synthesis, and then an abasic site can be generated using uracil DNA glycosylase (UDG) for deoxyuridine, FPG glycosylase for 8-oxoguanine, and AlkA glycosylase for deoxyinosine. The polynucleotide strand including the abasic site can then be cleaved by treatment with endonuclease (e.g., endoIV endonuclease, AP lyase, FPG glycosylase/AP lyase, Endo VIII glycosylase/AP lyase), heat or alkali. Additionally or alternatively, cleavage strategies can include use of ribonucleotides, photochemical cleavage, hemimethylated DNA, or PCR stoppers, as described in the incorporated materials of U.S. Pat. No. 8,715,966.

Following the cleavage step, the amplification product of the initial amplification process comprises an immobilized strand and a non-immobilized strand, and the non-immobilized strand can be then further amplified using the remaining primers immobilized on the solid support. For example, as shown in FIG. 1, the double-stranded amplification product is subjected to partially denaturing conditions to facilitate hybridization of a portion of the non-immobilized strand (shown as P7') to an unextended primer (P7). The P7 primer can then be extended by a polymerase under conditions suitable for extension, thus generating a new copy of the non-immobilized template strand. The steps of partial denaturing the template, hybridization to a new, unextended primer, and extension can be repeated as many times as desired. The process can be repeated many times until the available surface primers are substantially used up. In some embodiments, cycling through the process can be controlled, for example, via chemical denaturing or temperature cycling. In some embodiments, cycling continues under conditions that allow the process to be repeated continuously, without the need for cycling temperature of chemical conditions. Thus, the steps of partial denaturing the template, and hybridization to the immobilized primer can occur using any one of number of methods known in the art. For example, in some embodiments, recombinase primer amplification (RPA) is used to facilitate strand invasion and subsequent extension of immobilized primers. Methods and components for use in RPA are described in U.S. Pat. Nos. 5,223,414 and 7,399,590, and U.S. Publication 2013/0225421, the content of each which is incorporated by reference in its entirety.

A reagent for use in RPA can include further components that facilitate amplicon formation and in some cases increase the rate of amplicon formation. An example is a recombinase. Recombinase can facilitate amplicon formation by allowing repeated invasion/extension. More specifically, recombinase can facilitate invasion of a target nucleic acid by the polymerase and extension of a primer by the polymerase using the target nucleic acid as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590, each of which is incorporated herein by reference.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, Mass.). Further, examples of useful formulations that include a helicase protein are described in U.S. Pat. Nos. 7,399,590 and 7,829,284, each of which is incorporated herein by reference. Additionally or alternatively, topoisomerase can be used in a similar manner as helicase and/or recombinase.

Alternatively or additionally to the RPA methodology described above, the steps of partially denaturing and hybridizing the template to a new immobilized primer can occur using template walking technology. In some embodiments, template walking uses low Tm of the surface oligo (typically >60% AT primer) to facilitate breathing of the ends of the DNA so that a strand can walk from primer to primer. Methods for designing surface oligonucleotides and conditions for template walking are described in the incorporated materials of U.S. Publication 2013/0225421.

Alternatively or additionally to RPA and template walking, the steps of partially denaturing and hybridizing the template to a new immobilized primer can occur using cyclical methodologies to cycle between denaturing and hybridization conditions. For example, temperature cycling, and cycling of chemical denaturants and the like are known in the art and can be used in the methods presented herein.

Figure 2:
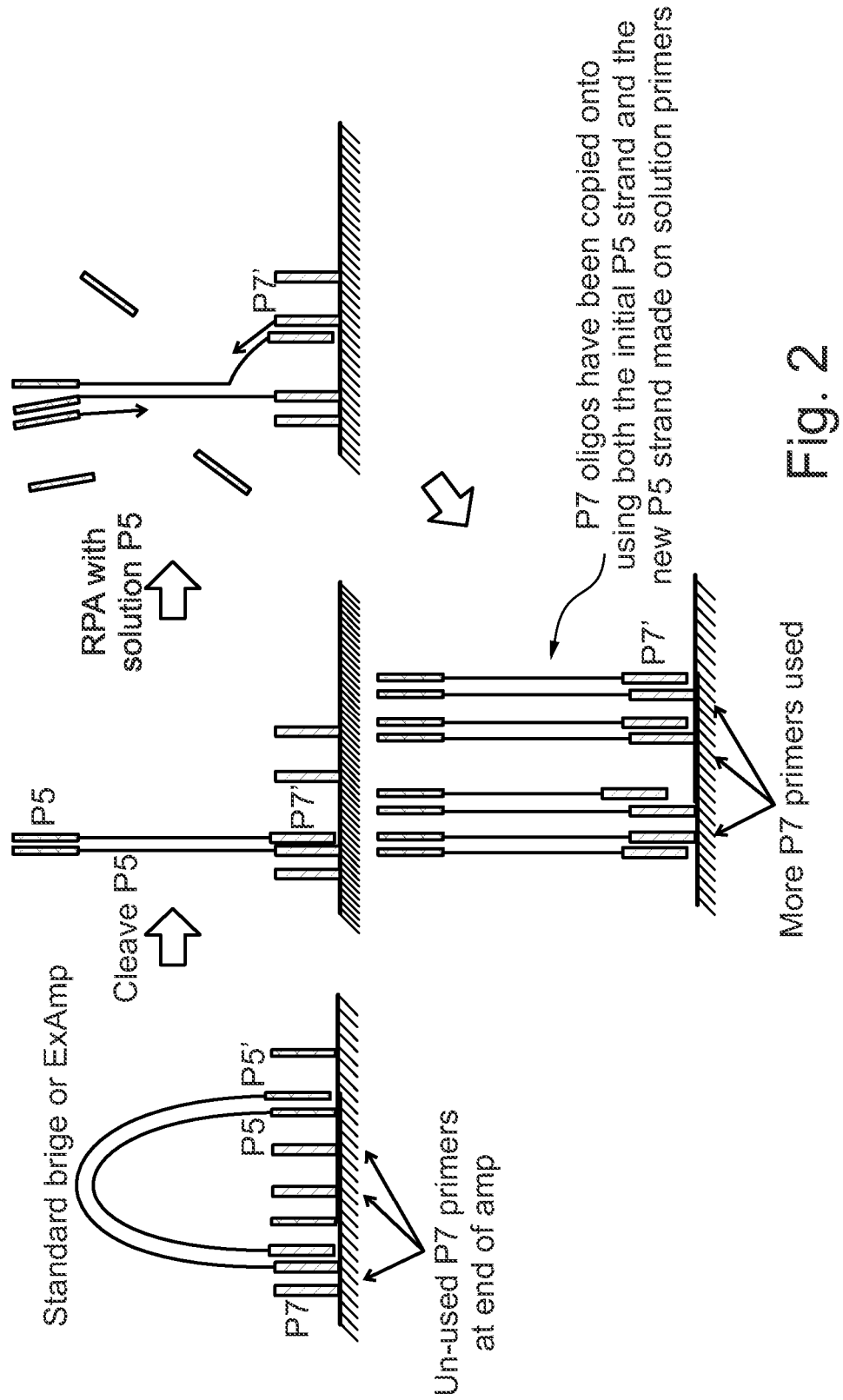
FIG. 2 is a schematic showing an amplification method according to one embodiment.

Additionally or alternatively to the embodiments described above, a solution primer can be provided in the RPA mix to form template/primer duplexes in solution. One example is illustrated in FIG. 2. As shown in FIG. 2, after cleavage of one of the primer sets (P5), RPA is performed in the presence of P5 primers in solution. Thus, extension occurs from both ends of the template. One extension reaction is carried out to extend the immobilized P7 primers. In addition, strand invasion, hybridization and extension is carried out to extend the solution-phase P5 primers to form a complementary copy of the immobilized strands. This will then form extra copies of the P5 strand which can be used to better occupy the P7 primers and accelerate amplification, as shown in FIG. 2. In certain embodiments, a new set of primers is added in solution. In some embodiments, the cleaved primers are collected after the cleavage reaction and are used in solution to facilitate the amplification.

The methods described above are further described in the figures and examples below. In the figures and examples, the term "sideways boost" refers to cleavage of one of the surface primers, followed by a second round of amplification using the remaining immobilized primer. In some embodiments, sideways boost is performed with added primer in solution.

The second round of amplification being proposed here has some similarities to the template walking amplification technology described in the incorporated materials of U.S. Publication 2013/0225421, also referred to as "wildfire" amplification. However, several are important differences are described below. Wildfire uses template walking to do the entire amplification of the surface DNA from a single molecule. In contrast, the proposed amplification scheme is used as an additional intensity boost, to further amplify the 100's-1000's of molecules within a cluster which have already been made by 2 primer surface amplification. Thus, the resulting clusters are much more dense with amplification product, and imaging of the nucleotides in the clusters is many times more robust than what would be expected using either bridge amplification alone or wildfire amplification alone. Indeed, it is counterintuitive to cleave one of the primers used in surface amplification, because it would be expected that amplification using both forward and reverse primers would proceed exponentially, compared to a linear amplification with a single immobilized primer. As evidenced in the Example section below, it has been surprisingly discovered that combining standard bridge or ExAmp surface amplification with cleavage of one of the primers, followed by a sideways boost, yields amplification product that is many times more robust, enabling significantly higher utilization of surface primers and generating clusters that are many times brighter during optical scanning analysis. It was unexpected that enhanced occupancy would result from cleavage of one of the bridge amplification primers.

Embodiments for Paired End Sequencing

Some sequencing methodologies include paired end sequencing, involving a second sequencing read on the opposite strand of the first read, for example as described in U.S. Pat. Nos. 7,754,429 and 8,017,335, each of which is incorporated herein by reference. In typical embodiments, paired end methods take advantage of two surface-bound primers to generate a copy of a sequenced strand. This process of regenerating a complementary strand is often referred to as a paired-end turn. However, in the methods described above, one of the two primer types is cleaved from the surface of the solid support, and paired end approaches may not be possible using traditional techniques.

As an alternative to regenerating a complementary strand, an alternative approach could be used in conjunction with the amplification methods described herein, such as any one of those approaches described in U.S. Pat. No. 8,192,930 which is incorporated herein by reference.

Also provided herein is an alternative method for generating a complementary strand for a second read. In some embodiments, the method can comprise providing a third surface primer that is blocked throughout all of the amplification steps, but is unblocked prior to generating the paired-end turn. The complementary sequence to this additional surface primer could, for example, be present in the adapters for the libraries, but would simply be amplified along with the inserts during cluster amplification. Only after unblocking of the surface primer, would it then become available for generating the paired-end turn molecules.

Figure 5:
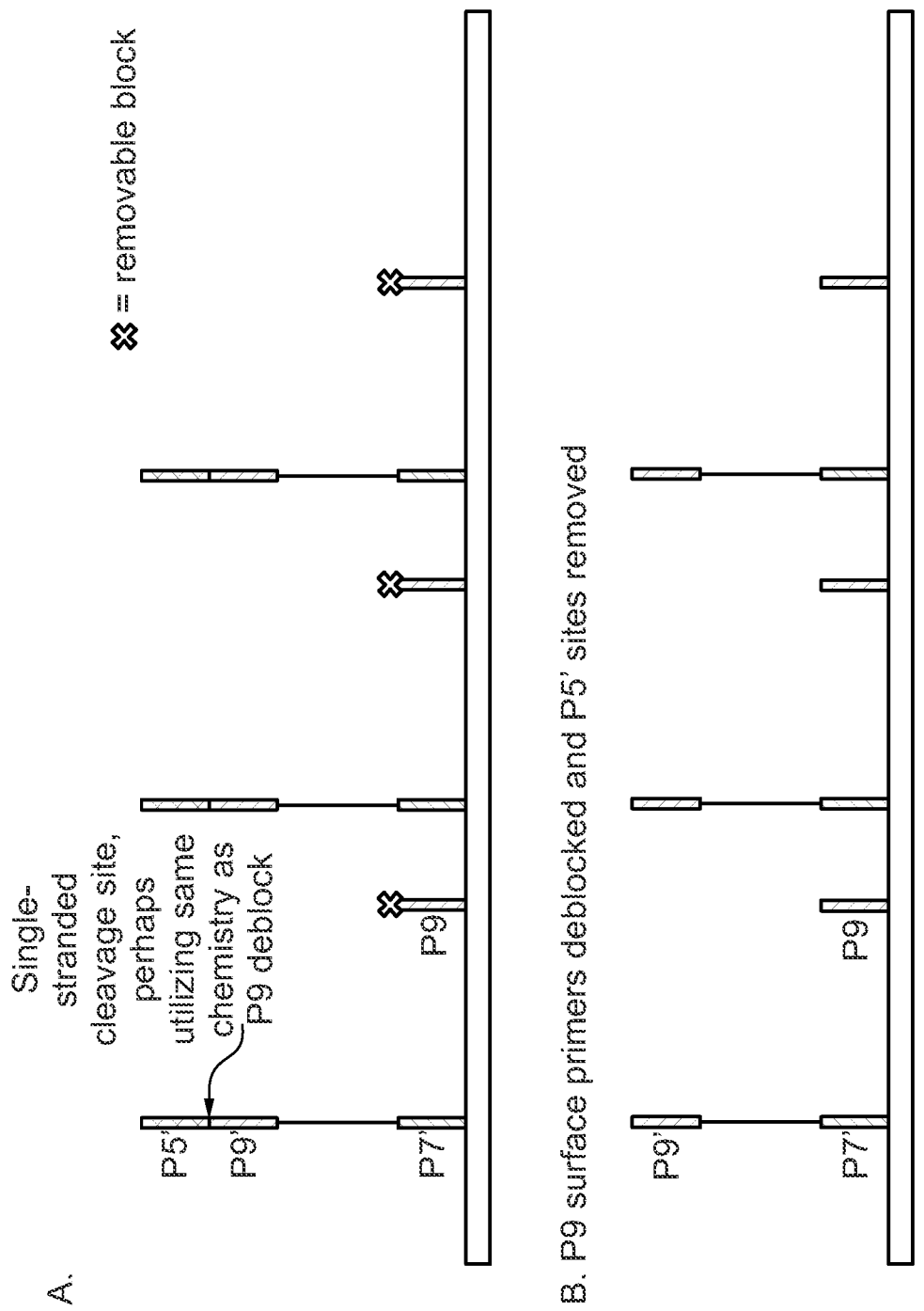
FIG. 5 is a schematic showing an alternative approach for generating a paired end turn.
Figure 6:
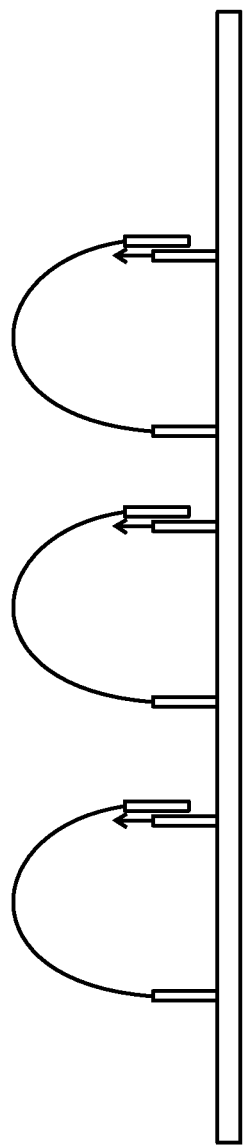
FIG. 6 is a schematic showing additional steps in the approach shown in FIG. 5.
Figure 6:
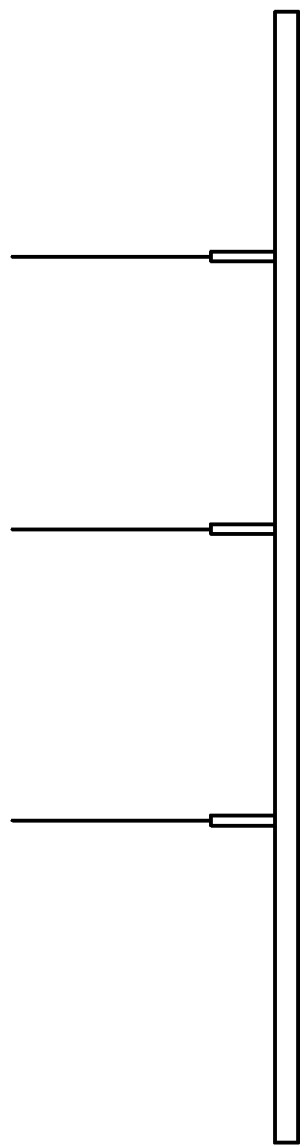

FIGS. 5 and 6 illustrate one implementation of this paired-end turn method. As illustrated in FIG. 5, a third amplification primer (designated as P9) is present on the solid support throughout the clustering process, but having a reversible 3' block that prevents extension under conditions suitable for amplification. As shown in the figure, the library also includes adapters that comprise the complement of P9 (designated as P9') positioned between the P5' adapter sequence and the internal portion to be sequenced. A cleavage site, able to be cleaved when single stranded, is also positioned in the adapter portion, between the P9' and P5' adapter sequences. Thus, after the first sequencing read is completed, the 3' block is removed from the P9 primers and the cleavable site is cleaved, releasing the P5' sequence. The resulting cleavage and deblocking product is illustrated in panel B of FIG. 5. Moving now to FIG. 6, the P9' adapter sequence can hybridize to the P9 primers on the surface, and a complementary strand can be regenerated, as is typically performed in paired-end turn methodologies.

Attachment of Oligonucleotides to Solid Supports

In the methods and compositions presented herein, polynucleotides are immobilized to the solid support. In some embodiments, the polynucleotides are covalently immobilized to the support. When referring to immobilization of molecules (e.g. nucleic acids) to a solid support, the terms "immobilized" and "attached" are used interchangeably herein and both terms are intended to encompass direct or indirect, covalent or non-covalent attachment, unless indicated otherwise, either explicitly or by context. In certain embodiments of the invention covalent attachment may be preferred, but generally all that is required is that the molecules (e.g. nucleic acids) remain immobilized or attached to the support under the conditions in which it is intended to use the support, for example in applications requiring nucleic acid amplification and/or sequencing.

Certain embodiments of the invention may make use of solid supports comprised of an inert substrate or matrix (e.g. glass slides, polymer beads etc.) which has been functionalized, for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass, particularly polyacrylamide hydrogels as described in WO 2005/065814 and US 2008/0280773, the contents of which are incorporated herein in their entirety by reference. In such embodiments, the biomolecules (e.g. polynucleotides) may be directly covalently attached to the intermediate material (e.g. the hydrogel) but the intermediate material may itself be non-covalently attached to the substrate or matrix (e.g. the glass substrate). The term "covalent attachment to a solid support" is to be interpreted accordingly as encompassing this type of arrangement.

Exemplary covalent linkages include, for example, those that result from the use of click chemistry techniques. Exemplary non-covalent linkages include, but are not limited to, non-specific interactions (e.g. hydrogen bonding, ionic bonding, van der Waals interactions etc.) or specific interactions (e.g. affinity interactions, receptor-ligand interactions, antibody-epitope interactions, avidin-biotin interactions, streptavidin-biotin interactions, lectin-carbohydrate interactions, etc.). Exemplary linkages are set forth in U.S. Pat. Nos. 6,737,236; 7,259,258; 7,375,234 and 7,427,678; and US Pat. Pub. No. 2011/0059865 A1, each of which is incorporated herein by reference.

In some embodiments, the solid support comprises a patterned surface. A "patterned surface" refers to an arrangement of different regions in or on an exposed layer of a solid support. For example, one or more of the regions can be features where one or more amplification primers are present. The features can be separated by interstitial regions where amplification primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. Exemplary patterned surfaces that can be used in the methods and compositions set forth herein are described in U.S. Ser. No. 13/661,524 or US Pat. App. Publ. No. 2012/0316086 A1, each of which is incorporated herein by reference.

In some embodiments, the solid support comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface can be wells in an array of wells (e.g. microwells or nanowells) on glass, silicon, plastic or other suitable solid supports with patterned, covalently-linked gel such as poly(N-(5-azidoacetamidylpentyl) acrylamide-co-acrylamide) (PAZAM, see, for example, U.S. Prov. Pat. App. Ser. No. 61/753,833, which is incorporated herein by reference). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However in many embodiments, the gel need not be covalently linked to the wells. For example, in some conditions silane free acrylamide (SFA, see, for example, US Pat. App. Pub. No. 2011/0059865 A1, which is incorporated herein by reference) which is not covalently attached to any part of the structured substrate, can be used as the gel material.

In particular embodiments, a structured substrate can be made by patterning a solid support material with wells (e.g. microwells or nanowells), coating the patterned support with a gel material (e.g. PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of target nucleic acids (e.g. a fragmented human genome) can then be contacted with the polished substrate such that individual target nucleic acids will seed individual wells via interactions with primers attached to the gel material; however, the target nucleic acids will not occupy the interstitial regions due to absence or inactivity of the gel material. Amplification of the target nucleic acids will be confined to the wells since absence or inactivity of gel in the interstitial regions prevents outward migration of the growing nucleic acid colony. The process is conveniently manufacturable, being scalable and utilizing conventional micro- or nano-fabrication methods.

Amplification and Clustering

For example, in some embodiments, the immobilized DNA fragments are amplified using cluster amplification methodologies as exemplified by the disclosures of U.S. Pat. Nos. 7,985,565 and 7,115,400, the contents of each of which is incorporated herein by reference in its entirety. The incorporated materials of U.S. Pat. Nos. 7,985,565 and 7,115,400 describe methods of solid-phase nucleic acid amplification which allow amplification products to be immobilized on a solid support in order to form arrays comprised of clusters or "colonies" of immobilized nucleic acid molecules. Each cluster or colony on such an array is formed from a plurality of identical immobilized polynucleotide strands and a plurality of identical immobilized complementary polynucleotide strands. The arrays so-formed are generally referred to herein as "clustered arrays". The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, preferably via a covalent attachment. Cluster amplification methodologies are examples of methods wherein an immobilized nucleic acid template is used to produce immobilized amplicons. Other suitable methodologies can also be used to produce immobilized amplicons from immobilized DNA fragments produced according to the methods provided herein. For example one or more clusters or colonies can be formed via solid-phase PCR whether one or both primers of each pair of amplification primers are immobilized.

In other embodiments, the immobilized DNA fragments are amplified in solution. For example, in some embodiments, the immobilized DNA fragments are cleaved or otherwise liberated from the solid support and amplification primers are then hybridized in solution to the liberated molecules. In other embodiments, amplification primers are hybridized to the immobilized DNA fragments for one or more initial amplification steps, followed by subsequent amplification steps in solution. Thus, in some embodiments an immobilized nucleic acid template can be used to produce solution-phase amplicons.

Sequencing Methods

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199, PCT Publication No. WO 07/010,251, U.S. Patent Application Publication No. 2012/0270305 and U.S. Patent Application Publication No. 2013/0260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Application Publication No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Patent Application Publication No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due to the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm², 50,000 features/cm², 100,000 features/cm², 1,000,000 features/cm², 5,000,000 features/cm², or higher.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in US 2010/0111768 A1 and U.S. Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. Ser. No. 13/273,666, which is incorporated herein by reference.

EXAMPLE 1

Comparative Analysis of Amplification Methods with First Cycle of Sequencing

This example describes a comparison of standard ExAmp amplification to other methods that include a subsequent primer cleavage event and amplification under partial denaturing conditions, with or without the addition of primer in solution.

A standard single read HiSeq flowcell (Illumina) was seeded with 2 pM of CT9814 human genomic library. Clusters were generated by v1 ExAmp (Illumina, PCX1/2/3) with 15 minutes of amplification. Lanes were treated with periodate to linearize the P5 by cleaving the diol linker, thus completely removing the P5 primer. The clusters were then treated for signal boost by heating to 38° C. and then flushing with Illumina's v1 ExAmp reagents (lane 2) or ExAmp reagents and P5/SBS3 oligo (lane 3) for 10 min. Lane 1 was not further treated and used as control (no ExAmp control). The flow cell was stained with SYBR Green (Molecular Probes, 1/5000 dilution in 0.1M Tris/0.1M sodium ascorbate) and imaged on a fluorescence microscope.

Figure 3:
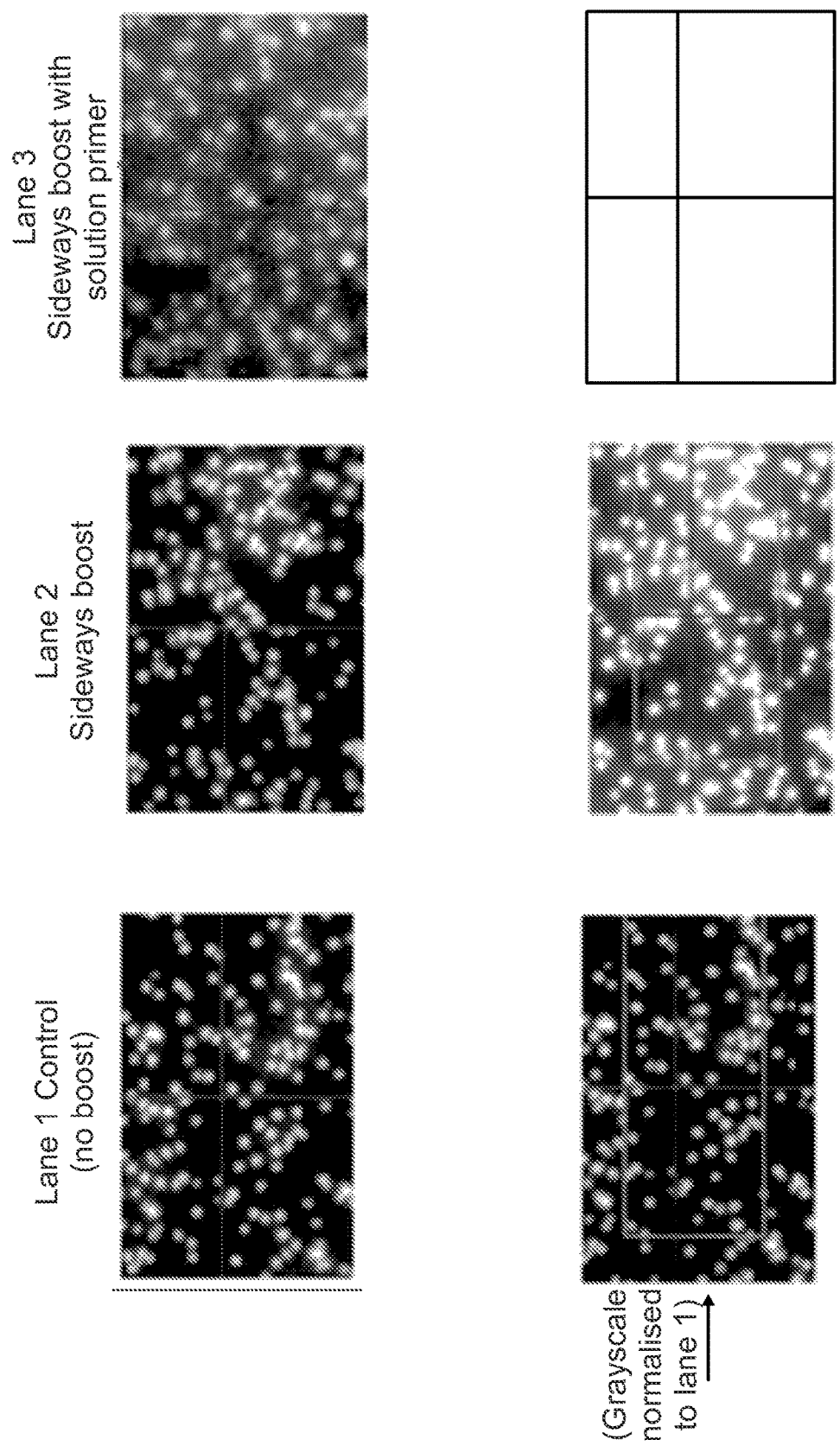
FIG. 3 shows comparative results of SyBr Green staining clusters amplified according to various methods.

As shown in the top panel of FIG. 3, the clusters in the control lane 1 were normal clusters with normal intensity, whereas removing the surface P5 primer and performing a further incubation with ExAmp was shown to result in brighter clusters, as highlighted by normalizing the gray scale to lane 1 (lane 2, FIG. 3 bottom panel). Lane 3 showed extra amplification occurring outwards from the original clusters as indicated by the white-out result seen after grayscale normalization.

Thus, the clusters subjected to sideways boost appear to have significantly higher amplification product in each cluster, generating a much more robust fluorescent signal.

EXAMPLE 2

Comparative Analysis of Amplification Methods with First Cycle of Sequencing

Figure 4:
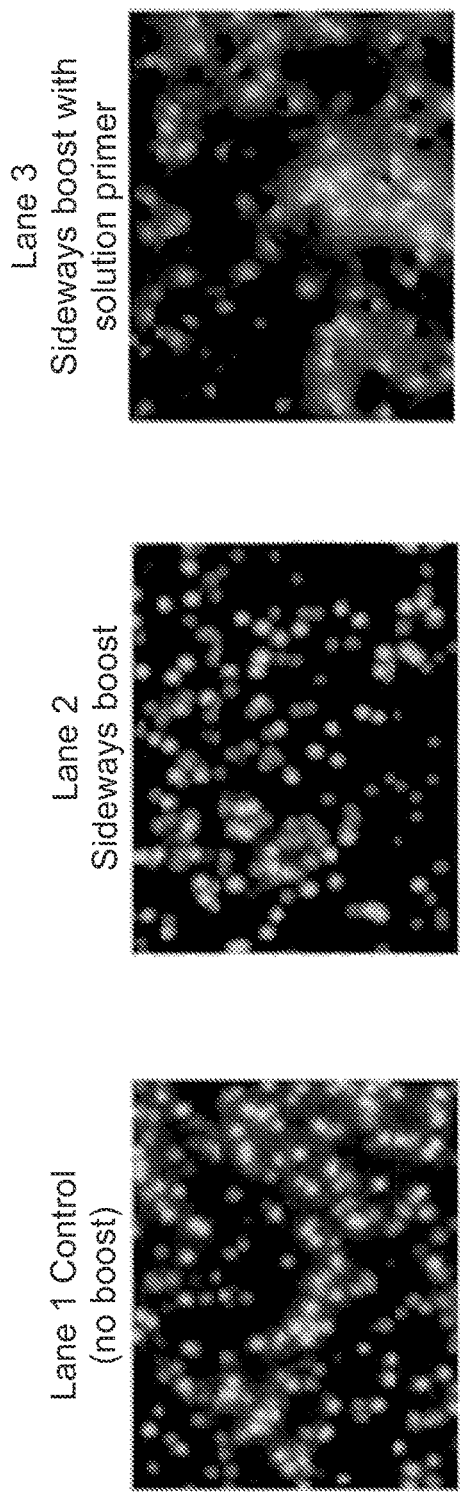
FIG. 4 shows comparative results clusters amplified according to various methods. Top panel shows imaging scan after $1^{st}$ cycle of nucleotide incorporation. Bottom panel shows Cy3 and Cy5 staining of clusters in each lane.
Figure 4:
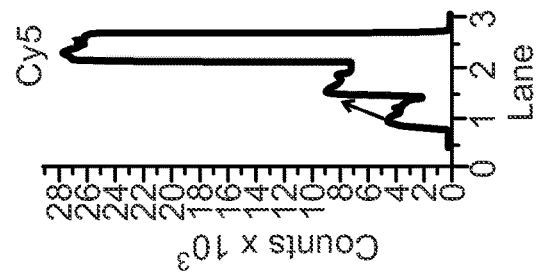
Figure 4:
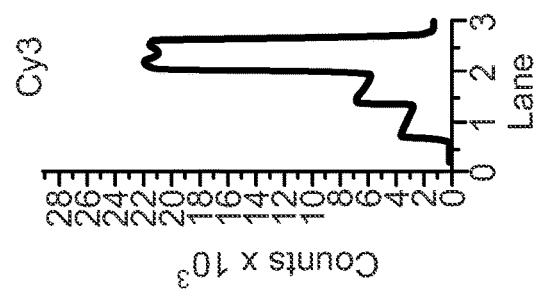
Figure 4:
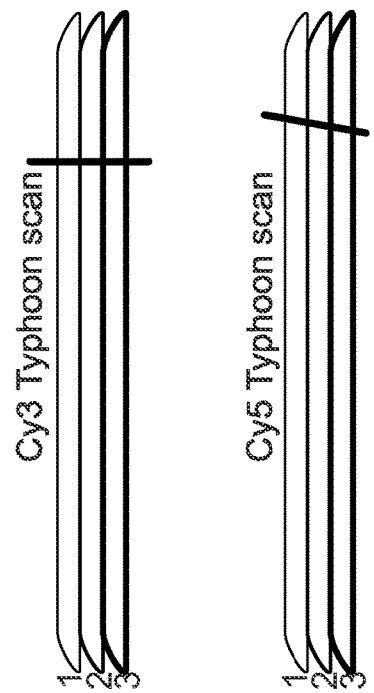

Following the analysis described in Example 1 above, the flowcell was then prepared to do a first cycle of sequencing incorporation by hybridizing a sequencing primer and flushing over Illumina Incorporation mix IMX at 55 C for 5 minutes. Incorporation mix includes polymerase, and a labeled mix of 3'-blocked dNTPs. After washing with Illumina wash buffer PR2, a scan mix of 0.1M Tris/0.1M sodium ascorbate was flushed into the flowcell and 1st cycle images were taken on a fluorescence microscope, as shown on FIG. 4. A further imaging analysis was performed by quantitating Cy3 and Cy5 staining of the clusters in each lane. As shown in the bottom panel of FIG. 4, quantitation shows that sideways boost alone (lane 2) generates clusters that are at least 2× brighter compared to control. Sideways boost with solution primer (lane 3) yields clusters that are more than 6× brighter compared to control.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A method of preparing immobilized templates for a nucleic acid sequencing reaction comprising:
    (a) providing a solid support having a plurality of forward and reverse amplification primers immobilized thereon, wherein a subset of said plurality of amplification primers comprises a cleavage site;
    (b) amplifying a target nucleic acid template using the subset of amplification primers on the solid support to produce a plurality of double-stranded nucleic acid molecules, wherein both strands of each double-stranded nucleic acid molecule are attached to the solid support at their 5' ends;
    (c) cleaving the subset of amplification primers at the cleavage site to produce a linearized amplification product comprising a cleaved non-immobilized strand and a complementary immobilized strand; and
    (d) subjecting the amplification product to partially-denaturing conditions to facilitate hybridization of a 3' terminal portion of the cleaved non-immobilized strand with a complementary immobilized amplification primer, followed by extension of the immobilized amplification primer to generate an immobilized copy of the non-immobilized strand of the amplification product.

2. The method of claim 1, wherein the partially-denaturing conditions comprise adding one or more components of a recombinase/polymerase amplification reaction to facilitate strand invasion.

3. The method of claim 1, wherein the partially-denaturing conditions comprise subjecting the template to conditions suitable for template walking.

4. The method of claim 1, wherein step (d) comprises applying forward or reverse amplification primers in solution to facilitate hybridization of the solution amplification primers to the non-immobilized end of the complementary immobilized strand of the amplification product.

5. The method of claim 4, wherein the subset of amplification primers on the solid support comprises forward amplification primers.

6. The method of claim 5, wherein step (d) comprises applying forward amplification primers in solution to facilitate hybridization of the solution forward amplification primers to the non-immobilized end of the complementary immobilized strand of the amplification product.

7. The method of claim 4, wherein the subset of amplification primers comprises reverse amplification primers.

8. The method of claim 7, wherein step (d) comprises applying reverse amplification primers in solution to facilitate hybridization of the solution reverse amplification primers to the non-immobilized end of the complementary immobilized strand of the amplification product.

9. The method of claim 1, further comprising sequencing the target nucleic acid.

10. The method of claim 9, wherein sequencing the target nucleic acid comprises:
hybridizing one or more sequencing primers to an immobilized nucleic acid strand;
extending the one or more sequencing primers by incorporating one or more labeled nucleotides into a nascent strand; and
detecting the labeled nucleotides, thereby obtaining sequence information about the target nucleic acid.

11. The method of claim 1, wherein said solid support is planar.

12. The method of claim 1, wherein said solid support comprises microwells.

13. The method of claim 1, wherein said target nucleic acid has a length of at least 10, 20, 50, 100, 200 or at least 500 nucleotides.

14. The method of claim 1, wherein the subset of amplification primers on the solid support are the forward amplification primers.

15. The method of claim 1, wherein the subset of amplification primers on the solid support are the reverse amplification primers.

* * * * *